United States Patent
Staley et al.

(10) Patent No.: US 10,105,899 B2
(45) Date of Patent: Oct. 23, 2018

(54) IV MEMBRANE ATTACHMENT SYSTEMS AND METHODS

(71) Applicant: Becton, Dickinson and Company, Franklin Lakes, NJ (US)

(72) Inventors: Shaun Staley, Sandy, UT (US); Justin G. Hortin, Farmington, UT (US); Brent R. Stoddard, Roy, UT (US); Jason Rivkowich, Draper, UT (US); Lawrence J. Trainer, Murray, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 394 days.

(21) Appl. No.: 15/078,718

(22) Filed: Mar. 23, 2016

(65) Prior Publication Data
US 2016/0279860 A1   Sep. 29, 2016

Related U.S. Application Data

(60) Provisional application No. 62/138,712, filed on Mar. 26, 2015.

(51) Int. Cl.
*B32B 37/00* (2006.01)
*B29C 65/08* (2006.01)
(Continued)

(52) U.S. Cl.
CPC .......... *B29C 65/08* (2013.01); *A61M 5/1411* (2013.01); *A61M 5/38* (2013.01); *B29C 65/1635* (2013.01);
(Continued)

(58) Field of Classification Search
CPC ....... A61M 5/1411; A61M 5/38; B29C 65/08; B29C 65/1635; B29C 65/1654;
(Continued)

(56) References Cited

U.S. PATENT DOCUMENTS 2,129,983 A   9/1938   Bacon
2,729,212 A   1/1956   Butler
(Continued)

FOREIGN PATENT DOCUMENTS

AU   171431 B2   3/2004
CA   2 460 251 A1   4/2003
(Continued)

OTHER PUBLICATIONS

Braun, Product Detail, the URL retrieved from http://www.bbraunoem-industrial.com/products/details.cfm?prodid=B0843225&ie-Caps &area=C, p. 1 (Apr. 12, 2005).
(Continued)

*Primary Examiner* — James D Sells
(74) *Attorney, Agent, or Firm* — Craig Metcalf; Jeanne Lukasavage; Kirton McConkie

(57) ABSTRACT

An intravenous delivery system may have a liquid source containing a liquid, tubing, and an anti-run-dry membrane positioned such that the liquid, flowing form the liquid source to the tubing, passes through the anti-run-dry membrane. The anti-run-dry membrane may be positioned within an exterior wall of a drip unit, and may have a weld surface secured to a seat of the exterior wall via application of compression to press the weld surface against the seat, and application of coherent light or vibration. In response to application of the coherent light or vibration, localized melting may occur, causing the weld surface to adhere to the seat. The anti-run-dry membrane may be modified to have a melting point close to that of the seat. Ultrasonic or laser welding may be applied in a manner that causes portions of the seat to melt and flow into pores of the weld surface.

20 Claims, 6 Drawing Sheets

(51) Int. Cl.
*A61M 5/14* (2006.01)
*A61M 5/38* (2006.01)
*B29C 65/16* (2006.01)
*B29C 65/00* (2006.01)
*B29L 31/00* (2006.01)
*B29L 23/00* (2006.01)

(52) U.S. Cl.
CPC ...... *B29C 65/1654* (2013.01); *B29C 65/1664* (2013.01); *B29C 66/112* (2013.01); *B29C 66/131* (2013.01); *B29C 66/232* (2013.01); *B29C 66/24221* (2013.01); *B29C 66/30223* (2013.01); *B29C 66/30326* (2013.01); *B29C 66/322* (2013.01); *B29C 66/5344* (2013.01); *B29C 66/5346* (2013.01); *B29C 66/61* (2013.01); *B29C 66/612* (2013.01); *B29C 66/652* (2013.01); *B29C 66/712* (2013.01); *B29C 66/727* (2013.01); *B29C 66/73116* (2013.01); *B29C 66/73161* (2013.01); *B29C 66/73171* (2013.01); *B29C 66/73921* (2013.01); *B29C 66/81431* (2013.01); *B29C 65/1616* (2013.01); *B29C 65/1677* (2013.01); *B29C 66/026* (2013.01); *B29C 66/229* (2013.01); *B29C 66/71* (2013.01); *B29C 66/8322* (2013.01); *B29C 66/9513* (2013.01); *B29L 2023/007* (2013.01); *B29L 2031/753* (2013.01); *B29L 2031/7546* (2013.01)

(58) Field of Classification Search
CPC . B29C 65/1664; B29C 66/112; B29C 66/131; B29C 66/232; B29C 66/24221; B29C 66/30223; B29C 66/30326; B29C 66/322; B29C 66/5344; B29C 66/5346; B29C 66/61; B29C 66/612; B29C 66/652; B29C 66/712; B29C 66/727; B29C 66/73116; B29C 66/73161; B29C 66/7317; B29C 66/73921; B29C 66/81431
USPC ...................................................... 156/73.1
See application file for complete search history.

(56) References Cited

U.S. PATENT DOCUMENTS

| | | | |
|---|---|---|---|
| 2,954,028 A | 9/1960 | Smith | |
| 3,030,954 A | 4/1962 | Thornton, Jr. | |
| 3,390,677 A | 7/1968 | Razimbaud | |
| 3,557,786 A | 1/1971 | Barr, Sr. et al. | |
| 3,631,654 A | 1/1972 | Riely et al. | |
| 3,722,697 A | 3/1973 | Burke et al. | |
| 3,744,492 A | 7/1973 | Leibinsohn | |
| 3,756,233 A | 9/1973 | Goldowsky | |
| 3,782,083 A | 1/1974 | Rosenberg | |
| 3,806,386 A | 4/1974 | Burke et al. | |
| 3,931,818 A | 1/1976 | Goldowsky | |
| 4,013,072 A | 3/1977 | Jess | |
| 4,034,754 A | 7/1977 | Virag | |
| 4,066,556 A | 1/1978 | Vaillancourt | |
| 4,113,627 A | 9/1978 | Leason | |
| 4,121,584 A * | 10/1978 | Turner | A61M 5/16809 604/246 |
| 4,170,056 A | 10/1979 | Meyst et al. | |
| 4,198,971 A | 4/1980 | Noiles | |
| 4,200,095 A | 4/1980 | Reti | |
| 4,227,527 A | 10/1980 | De Frank et al. | |
| 4,243,032 A | 1/1981 | Howell | |
| 4,248,223 A | 2/1981 | Turner et al. | |
| 4,269,222 A | 5/1981 | Palti | |
| 4,276,170 A | 6/1981 | Vaillancourt | |
| 4,406,042 A | 9/1983 | McPhee | |
| 4,413,990 A | 11/1983 | Mittleman | |
| 4,428,743 A | 1/1984 | Heck | |
| 4,465,479 A | 8/1984 | Meisch | |
| 4,521,212 A * | 6/1985 | Ruschke | A61M 5/36 604/126 |
| 4,548,600 A | 10/1985 | Ruschke | |
| 4,571,244 A | 2/1986 | Knighton | |
| 4,583,979 A | 4/1986 | Palti | |
| 4,589,171 A | 5/1986 | McGill | |
| 4,601,712 A | 7/1986 | Cole et al. | |
| 4,610,781 A | 9/1986 | Bilstad et al. | |
| 4,615,694 A | 10/1986 | Raines | |
| 4,625,494 A | 12/1986 | Iwatschenko et al. | |
| 4,685,912 A | 8/1987 | Jones | |
| 4,795,429 A | 1/1989 | Feldstein | |
| 4,812,293 A | 3/1989 | McLaurin et al. | |
| 4,842,588 A | 6/1989 | Jones | |
| 4,952,210 A | 8/1990 | Alchas | |
| 4,997,149 A | 3/1991 | Koch | |
| 5,102,400 A | 4/1992 | Leibinsohn | |
| 5,131,537 A | 7/1992 | Gonzales | |
| 5,188,588 A | 2/1993 | Schoendorfer et al. | |
| 5,195,987 A | 3/1993 | Karpiak | |
| 5,308,314 A | 5/1994 | Fukui et al. | |
| 5,308,333 A | 5/1994 | Skakoon | |
| 5,309,604 A | 5/1994 | Poulsen | |
| 5,389,082 A | 2/1995 | Baugues et al. | |
| 5,419,770 A | 5/1995 | Crass et al. | |
| 5,423,346 A | 6/1995 | Daoud | |
| 5,423,769 A | 6/1995 | Jonkman et al. | |
| 5,435,448 A | 7/1995 | Kempen | |
| 5,489,385 A | 2/1996 | Raabe et al. | |
| 5,542,160 A | 8/1996 | Arndt | |
| 5,681,294 A | 10/1997 | Osborne et al. | |
| 5,735,826 A | 4/1998 | Richmond | |
| 5,776,109 A | 7/1998 | Urrutia | |
| 5,779,674 A | 7/1998 | Ford | |
| 5,836,923 A * | 11/1998 | Mayer | A61M 39/04 604/246 |
| 5,851,202 A | 12/1998 | Carlsson | |
| 5,891,096 A * | 4/1999 | Hyun | A61M 5/148 604/131 |
| 5,899,665 A | 5/1999 | Makino et al. | |
| 5,902,281 A | 5/1999 | Kraus et al. | |
| 5,906,598 A | 5/1999 | Giesler et al. | |
| 6,015,119 A | 1/2000 | Starchevich | |
| 6,099,512 A | 8/2000 | Urrutia | |
| 6,103,119 A | 8/2000 | Clements et al. | |
| 6,106,504 A | 8/2000 | Urrutia | |
| 6,149,631 A | 11/2000 | Haydel, Jr. | |
| 6,213,986 B1 | 4/2001 | Darling, Jr. | |
| 6,224,578 B1 | 5/2001 | Davis et al. | |
| 6,261,267 B1 | 7/2001 | Chen | |
| 6,283,945 B1 | 9/2001 | Bierman | |
| 6,336,916 B1 | 1/2002 | Bormann et al. | |
| 6,503,225 B1 | 1/2003 | Kirsch et al. | |
| RE38,145 E | 6/2003 | Lynn | |
| D479,328 S | 9/2003 | Reynolds et al. | |
| 6,833,488 B2 | 12/2004 | Bucevschi et al. | |
| 7,160,087 B2 | 1/2007 | Fathallah et al. | |
| 7,722,577 B2 | 5/2010 | Miner | |
| 7,892,204 B2 | 2/2011 | Kraus | |
| 8,282,046 B2 | 10/2012 | Harding et al. | |
| 8,523,829 B2 | 9/2013 | Miner et al. | |
| 2002/0156431 A1 | 10/2002 | Feith et al. | |
| 2003/0220616 A1 | 11/2003 | Kraus | |
| 2004/0011749 A1 | 1/2004 | Hutchinson et al. | |
| 2004/0254542 A1 | 12/2004 | Sacco | |
| 2005/0059926 A1 | 3/2005 | Sage, Jr. et al. | |
| 2005/0171491 A1 | 8/2005 | Minh Miner et al. | |
| 2005/0273062 A1 | 12/2005 | Franksson et al. | |
| 2006/0188407 A1 | 8/2006 | Gable et al. | |
| 2006/0283544 A1 | 12/2006 | Mori et al. | |
| 2008/0097333 A1 | 4/2008 | Henning | |
| 2011/0276010 A1 | 11/2011 | Davis et al. | |
| 2013/0224866 A1 | 8/2013 | Lurvey et al. | |
| 2013/0338588 A1 | 12/2013 | Grimm et al. | |
| 2013/0345658 A1 | 12/2013 | Browne et al. | |

(56) References Cited

U.S. PATENT DOCUMENTS

FOREIGN PATENT DOCUMENTS

| | | |
|---|---|---|
| CN | 201 088 751 Y | 7/2008 |
| CN | 101 732 767 | 6/2010 |
| CN | 203 107 819 U | 8/2013 |
| CN | 203 379 419 U | 1/2014 |
| DE | 41 42 625 A1 | 4/1993 |
| DE | 196 22 050 A1 | 12/1997 |
| EP | 0 001 114 A2 | 3/1979 |
| EP | 0 195 310 A1 | 9/1986 |
| EP | 0 229 354 A2 | 7/1987 |
| EP | 0 788 824 A3 | 11/1998 |
| EP | 1 181 065 B1 | 7/2003 |
| EP | 2 500 051 A1 | 9/2012 |
| FR | 2 160 821 A1 | 7/1973 |
| GB | 2 044 620 A | 10/1980 |
| JP | H10-127778 A | 5/1998 |
| JP | 2000-014745 A | 1/2000 |
| JP | 2000-229126 A | 8/2000 |
| WO | 96/29104 A1 | 9/1996 |
| WO | 99/22787 A1 | 5/1999 |
| WO | 00/66200 A1 | 11/2000 |
| WO | 01/41844 A1 | 6/2001 |
| WO | 03/028525 A2 | 4/2003 |
| WO | 2005/104776 A2 | 11/2005 |
| WO | 2005/118051 A2 | 12/2005 |
| WO | 2006/083359 A2 | 8/2006 |
| WO | 2007/079049 A2 | 7/2007 |
| WO | 2008/027157 A1 | 3/2008 |
| WO | 2009/046182 A1 | 4/2009 |
| WO | 2010/030602 | 3/2010 |
| WO | 2010/030602 A1 | 3/2010 |
| WO | 2011/139517 | 11/2011 |
| WO | 2011/139517 A1 | 11/2011 |
| WO | 2013/070337 A1 | 5/2013 |
| WO | 2013/188103 A1 | 12/2013 |

OTHER PUBLICATIONS

Braun, Product Detail, the URL retrieved from http://www.bbraunoem-industrial.com/products/ details.cfm?prodid=B0843225&id-Caps &area=C, p. 1 (Apr. 12, 2005).

Shift Labs, DripAssist Infusion Rate Monitor, http://www.shiftlabs.com/dripassist-human-health, pp. 1-5, Apr. 3, 2017.

\* cited by examiner

IV MEMBRANE ATTACHMENT SYSTEMS AND METHODS

RELATED APPLICATIONS

This application claims priority to U.S. Provisional Patent Application Ser. No. 62/138,712, filed Mar. 26, 2015, and entitled IV MEMBRANE ATTACHMENT SYSTEMS AND METHODS, which is incorporated herein in its entirety.

BACKGROUND

The present invention is generally directed to systems and methods for intravenous ("IV") delivery, by which fluids can be administered directly to a patient. More particularly, the present invention is directed systems and methods for manufacturing components of an intravenous delivery system. An intravenous delivery system according to the invention is used broadly herein to describe components used to deliver the fluid to the patient, for use in arterial, intravenous, intravascular, peritoneal, and/or non-vascular administration of fluid. Of course, one of skill in the art may use an intravenous delivery system to administer fluids to other locations within a patient's body.

One common method of administering fluids into a patient's blood flow is through an intravenous delivery system. In many common implementations, an intravenous delivery system may include a liquid source such as a liquid bag, a drip chamber used to determine the flow rate of fluid from the liquid bag, tubing for providing a connection between the liquid bag and the patient, and an intravenous access unit, such as a catheter that may be positioned intravenously in a patient. An intravenous delivery system may also include a Y-connector that allows for the piggybacking of intravenous delivery systems and for the administration of medicine from a syringe into the tubing of the intravenous delivery system.

It is a generally good practice to remove air from intravenous delivery systems that access a patient's blood flow. While this concern is critical when accessing arterial blood, it is also a concern when accessing the venous side. Specifically, if air bubbles are allowed to enter a patient's blood stream while receiving the intravenous administration of fluids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an intravenous delivery system for use in the intravenous administration of fluids, the complete removal of air bubbles can be a time consuming process. The process may also lead to contamination of the intravenous delivery system by inadvertently touching a sterile end of the intravenous delivery system. Typically, when an intravenous delivery system is primed, a clamp is closed to prevent fluid from moving from a drip chamber through the tubing. The intravenous delivery system may then be attached to an IV bag or bottle. Once attached, the drip chamber, which is typically made of a clear flexible plastic, may be squeezed to draw the fluid out of the IV bag or bottle and into the drip chamber. The drip chamber may be allowed to fill about ¼ to ½ full when the clamp is opened to allow fluid to flow through the tube to an end of the intravenous delivery system.

This initial process, however, typically traps air in tubing which must be removed. For example, the flow of the fluid through the tubing of the intravenous delivery system may be turbulent and can entrap air within the tube as the boundary layer between the fluid and the tubing is sheared. The flow rate out of the drip chamber may be higher than the flow rate of fluid entering the drip chamber. This can cause a bubble ladder to form as air is sucked from the drip chamber into the tubing.

Additionally, air bubbles may be generated as drops of fluid strike the surface of the pool of fluid within the drip chamber. These air bubbles can be pulled into the tubing of the IV set from the drip chamber. This problem may be aggravated in pediatric applications where the drip orifice may be smaller, which may result in increased turbulence.

To remove air bubbles from the intravenous delivery system, fluid from the IV bag or bottle may be allowed to flow through the tubing while an attendant taps the tubing to encourage the air bubbles out the end of the intravenous delivery system. As the fluid is allowed to flow out of the intravenous delivery system to clear air bubbles from the tubing, the fluid may be allowed to flow into a waste basket or other receptacle. During this procedure, the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the intravenous delivery system. More specifically, if the intravenous delivery system includes a Y-connector, air bubbles may be removed at the Y-connector by a syringe. This method still requires additional time and attention, and may also carry risk of contamination of the liquid to be delivered.

To address the difficulties of removing bubbles from an intravenous delivery system, various prior art intravenous delivery systems have employed a membrane for filtering air from the fluid as it flows through the intravenous delivery system. For example, oftentimes a membrane may be placed in the bottom of the drip chamber so that fluid flowing out of the drip chamber must pass through the membrane. The membrane can be configured to allow the passage of fluid while blocking the passage of air. In this way, bubbles are prevented from passing into the tubing leading to the patient. Similarly, a membrane can be included in the connector that couples the tubing to a catheter to block any air present in the tubing from passing into the patient's vasculature.

The use of air filtering membranes in these prior art intravenous delivery system designs have been beneficial. However, such membranes introduce new manufacturing challenges. Ordinary welding processes are typically used to attach materials with similar melting points together. The materials at the weld interface can be melted and thereby mixed together. However, membranes may be composed of materials with specific hydrodynamic properties, which may have melting points significantly different from those of the materials used in adjacent components of the intravenous delivery system. Thus, traditional welding techniques may not be effective for attaching the membrane in place.

Further, in order to extend the benefits of health care to lower income areas and individuals, it would be beneficial to reduce the manufacturing cost and complexity of processes used to make existing intravenous delivery systems. Yet further, increasing the reliability of such processes may reduce the risk that the intravenous delivery system will fail to operate properly due to a manufacturing defect.

BRIEF SUMMARY OF THE INVENTION

Embodiments of the present invention are generally directed to an intravenous delivery system with an anti-run-dry membrane. The intravenous delivery system may have a liquid source containing a liquid to be delivered to a patient, a drip unit containing the anti-run-dry membrane, and tubing. The tubing may have a first end connectable to the liquid source, and a second end connectable to a vent cap and/or an intravenous delivery unit.

The anti-run-dry membrane may be formed of a hydrophilic material, and may have a plurality of pores that permit the liquid to flow through the anti-run-dry membrane, while resisting passage of air through the anti-run-dry membrane. The anti-run-dry membrane may be secured to a seat formed on an exterior wall of the drip unit to prevent air from flowing from the top part of the drip unit to the bottom part of the drip unit, through the anti-run-dry membrane. The anti-run-dry membrane may be secured to the exterior wall through the use of a welding process, such as laser welding or ultrasonic welding.

The anti-run-dry membrane may be formed of Polyethersulfone (PES), which has a melting point significantly higher than that of the seat to which it is to be attached. This melting point differential may pose unique challenges for welding. In some embodiments, the material of the anti-run-dry membrane may be modified during fabrication of the anti-run-dry membrane through the use of a melting point reduction procedure. This may cause the anti-run-dry membrane to have a melting point significantly lower than that of the base material (for example, Polyethersulfone). The anti-run-dry membrane may have a melting point within 20° C. of the melting point of the material of which the seat is formed.

Additionally or alternatively, a unique laser welding procedure may be carried out. Laser welding may utilize a laser to direct coherent light at a laser impingement area on the juncture between the seat and the weld surface of the anti-run-dry membrane. The coherent light may optionally be directed through the exterior wall to reach the juncture. The exterior wall may have an opposing surface aligned with the seat and facing outward; the opposing surface may have a surface finished that provides the desired degree of scatter of the coherent light to ensure that the laser impingement area has the appropriate size. The laser impingement area may be moved along any of a variety of closed pathways to define a seal between the seat and the weld surface. A fixture may be used to provide compression prior to and/or during the laser welding process.

In alternative embodiments, a two-piece anti-run-dry membrane may be used to facilitate laser welding. The two-piece anti-run-dry membrane may have a membrane component and a welding component. The membrane component may provide the desired liquid permeability and air impermeability, while the welding component may be more readily weldable to the material of the exterior wall.

Additionally or alternatively, a unique ultrasonic welding procedure may be used to secure the weld surface to the seat. The seat may have an energy director that protrudes toward the weld surface. An ultrasonic welding horn may be advanced into the interior of the exterior wall, and into contact with the anti-run-dry membrane to press the weld surface against the seat. The ultrasonic welding horn may apply vibration to the juncture between the weld surface and the seat. The vibration may be concentrated in the energy director, which may preferentially melt and flow into the pores of the anti-run-dry membrane that are proximate the weld surface.

The anti-run-dry membrane may optionally have unequal pore sizes, for example, with larger pores proximate the weld surface. The larger pores may form a stronger bond by receiving a larger amount of melted material of the seat. In further alternative embodiments, two or more energy directors may be used, and may define a central relief between them. The ultrasonic welding horn may have a matching central relief that receives a thicker section of the anti-run-dry membrane and also receives flowable material from the energy directors to provide more secure attachment. In other alternatives, a seat may not have protruding energy directors, but may rather have a tapered shape or the like, in which a leading edge may act as an energy director. Such seat shapes may facilitate injection molding of the exterior wall.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention can be understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

Figure 1:
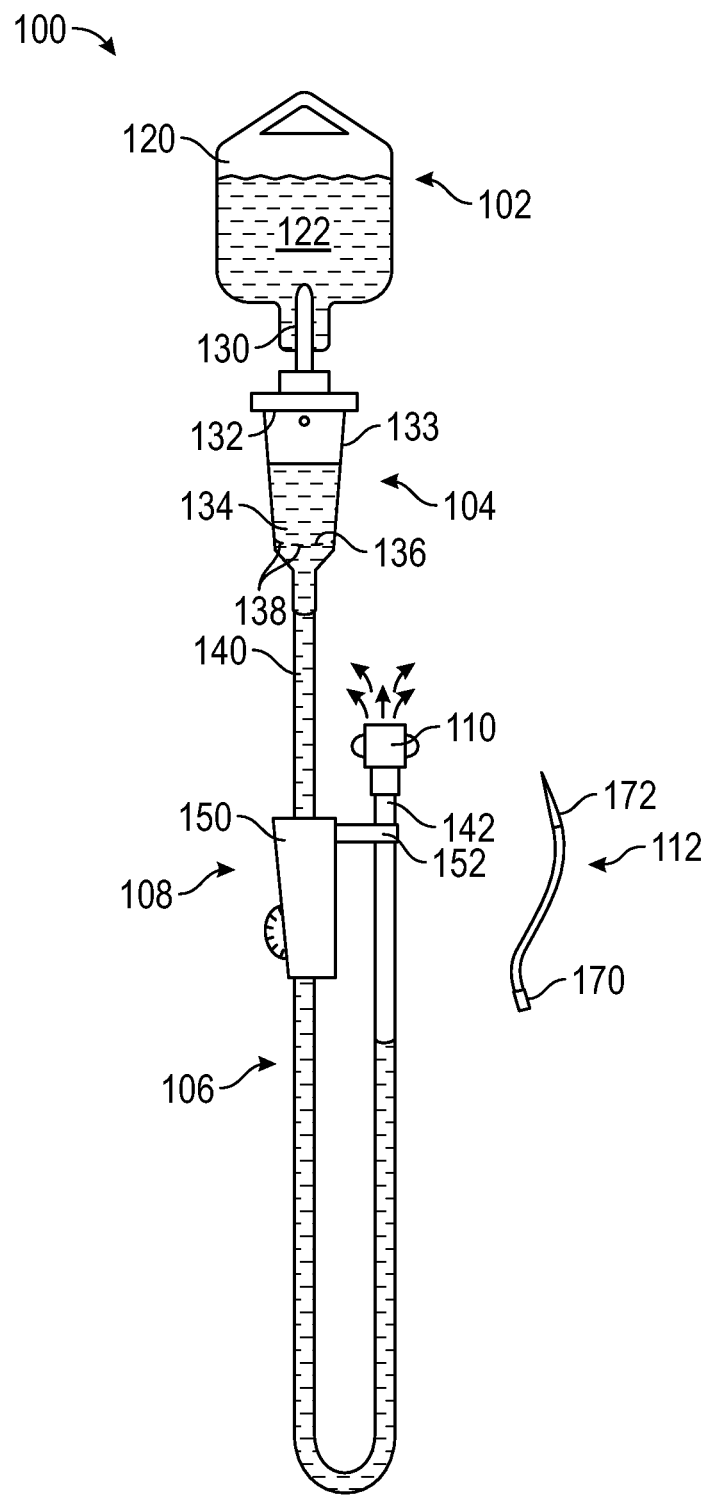
FIG. 1 is a front elevation view of an intravenous delivery system according to one embodiment.

Referring to FIG. 1, a front elevation view illustrates an intravenous delivery system 100 according to one embodiment. As shown, the intravenous delivery system 100 may have a number of components, which may include a liquid source 102, a drip unit 104, tubing 106 a retention unit 108, a vent cap 110, and an intravenous access unit 112. The manner in which these components are illustrated in FIG. 1 is merely exemplary; those of skill in the art will recognize that a wide variety of intravenous delivery systems exist. Thus, the various components the intravenous delivery system 100 may be omitted, replaced, and/or supplemented with components different from those illustrated.

The liquid source 102 may have a container containing a liquid 122 to be delivered intravenously to a patient. The liquid source 102 may, for example, have a membrane 120, which may be formed of a translucent, flexible polymer or the like. The membrane 120 may thus have a baglike configuration. The membrane 120 may be shaped to contain the liquid 122.

The drip unit 104 may be designed to receive the liquid 122 from the membrane 120 in a measured rate, for example, as a series of drips occurring at a predictable, consistent rate. The drip unit 104 may be positioned below the membrane 120 so as to receive the liquid 122 via gravity feed. The drip unit 104 may have a receiving device 130 that receives the liquid 122 from the liquid source 102, a drip feature 132 that determines the rate at which the liquid 122 is received by the drip unit 104, and an exterior wall 133 that defines a drip chamber 134 in which the liquid 122 is collected. An anti-run-dry membrane 136 may be positioned within the drip chamber 134 to enable a fluid column of significant length to be maintained within the tubing 106 after cessation of flow of the liquid 122 into the tubing 106, without permitting significant air to flow into the tubing 106 through the anti-run-dry membrane 136.

The tubing 106 may be standard medical grade tubing. The tubing 106 may be formed of a flexible, translucent material such as a silicone rubber. The tubing 106 may have a first end 140 and a second end 142. The first end 140 may be coupled to the drip unit 104, and the second end 142 may be coupled to the vent cap 110, such that the liquid 122 flows from the drip unit 104 to the vent cap 110, through the tubing 106.

The retention unit 108 may be used to retain various other components of the intravenous delivery system 100. As shown, the retention unit 108 may have a main body 150 and an extension 152. Generally, the tubing 106 may be connected to the main body 150 proximate the first end 140, and to the extension 152 proximate the second end 142. Various racks, brackets, and/or other features may be used in addition to or in place of the retention unit 108.

The vent cap 110 may be coupled to the second end 142 of the tubing 106. The vent cap 110 may have a vent, such as a hydrophilic membrane that is substantially permeable to air, but not to the liquid 122. Thus, air from within the vent cap 110 can be vented from the intravenous delivery system 100, with limited leakage of the liquid 122 from the intravenous delivery system 100.

The intravenous access unit 112 may be used to supply the liquid 122 to the vascular system of the patient. The intravenous access unit 112 may have a first end 170 and an access end 172. The first end 170 may be connectable to the second end 142 of the tubing 106 in place of the vent cap 110. Thus, when the intravenous delivery system 100 is fully primed, the intravenous access unit 112 may be coupled to the second end 142 of the tubing 106 in place of the vent cap 110. In alternative embodiments (not shown), various connectors such as Y-adapters may be used to connect the first end 170 of the intravenous access unit 112 to the tubing 106 without detaching the vent cap 110 from the second end 142 of the tubing 106.

The intravenous delivery system 100 may be primed by connecting the components (except for the intravenous access unit 112) together as illustrated in FIG. 1, and then allowing the liquid 122 to gravity feed through the drip unit 104 and the tubing 106 into the vent cap 110. If desired, the drip unit 104 may be squeezed or otherwise pressurized to expedite flow of the liquid 122 through the tubing 106.

As the liquid 122 flows through the tubing 106, air may become entrained in the liquid 122. This air may move from the first end 140 of the tubing 106, toward the second end 142 of the tubing 106, along with the column of liquid 122. This entrained air may gather into bubbles proximate the second end 142 of the tubing 106. The vent cap 110 may be designed to receive the liquid 122 to permit such air bubbles to be vented from the intravenous delivery system 100 through the vent cap 110.

Once the liquid 122 stops flowing into the liquid 122, for example, due to depletion of the liquid 122 in the liquid source 102, the anti-run-dry membrane 136 may act to restrict motion of air into the tubing 106. The anti-run-dry membrane 136 may have a plurality of pores 138, each of which has a size that causes the formation of a meniscus of the liquid 122 underneath the anti-run-dry membrane 136. Each meniscus may, via surface tension, contribute to the support of a column of the liquid 122 in the tubing 106. The anti-run-dry membrane 136 may be designed to facilitate support of a column of the liquid 122 of significant length before permitting air to enter the column. The longer the column that can be supported, the more robust the intravenous delivery system 100 will be to different operational conditions.

The anti-run-dry membrane 136 may be secured to the exterior wall 133 of the drip unit 104 through the use of various manufacturing methods. Although various welding techniques are known to be effective for securing plastic components together, such welding techniques often rely on the components having similar melting points so that they can melt together and intermix at the weld interface. Attachment of the anti-run-dry membrane 136 to the exterior wall 133 of the drip unit 104 may present a unique challenge due to the likely disparity in melting points between these two components.

More specifically, the exterior wall 133 of the drip unit 104 may be formed of any of a variety of materials such as PVC, SBC, and TPO. Such materials often have a melting point within the range of about 190° C. to about 210° C. By contrast, the anti-run-dry membrane 136 may be formed of a material such as Polyethersulfone (PES). In many formulations, PES may have a melting point within the range of about 250° C. to about 350° C. Accordingly, traditional fabrication techniques may not provide secure attachment of the anti-run-dry membrane 136 to the exterior wall 133. The exterior wall 133 may begin melting long before the anti-run-dry membrane 136 has reached its melting point; thus, the portion of the exterior wall 133 to which the anti-run-dry membrane 136 is to be attached may lose too much of its shape and rigidity before the anti-run-dry membrane 136 begins to melt.

In some embodiments, this disparity in melting points may be corrected by modifying the properties of the anti-run-dry membrane 136. For example, the melting point of the anti-run-dry membrane 136 may be lowered by altering the process used to manufacture the anti-run-dry membrane 136 in various ways. For example, the melting point of a PES material may be lowered by (1) changing the chemical composition of the ether pre-polymer to provide the pre-polymer with a more flexible chemical structure, resulting in a more flexible chemical structure of the PES material, (2) copolymerizing the PES with a more flexible material such as a polyether pre-polymer with multiple CH2 repeat units in the backbone of the chemical structure, and/or (3) adding side branching to increase free-volume and allow greater flexibility of the aromatic ring structure of the PES.

These are merely exemplary; those of skill in the art will recognize that the melting point of a PES material may be reduced in other ways besides those specifically set forth above. Further, the present disclosure is not limited to PES materials; rather, the melting point reduction processes set forth above may be applied to other materials that may be used in the formation of an anti-run-dry membrane. Such melting point reduction processes may be adapted as needed to the particular material(s) used to create the anti-run-dry membrane.

In some embodiments, the melting point of the anti-run-dry membrane 136 may be reduced to a level similar to that of the melting point of the exterior wall 133. In some examples, the melting point of the anti-run-dry membrane 136 may be reduced to within 50° C. of the melting point of the exterior wall 133. More precisely, the melting point of the anti-run-dry membrane 136 may be reduced to within 30° of the melting point of the exterior wall 133. Yet more precisely, the melting point of the anti-run-dry membrane 136 may be reduced to within 20° of the melting point of the exterior wall 133. Still more precisely, the melting point of the anti-run-dry membrane 136 may be reduced to within 10° of the melting point of the exterior wall 133.

In addition to or in the alternative to reduction of the melting point of the anti-run-dry membrane 136, welding processes may be tailored to the unique requirements of attachment of the anti-run-dry membrane 136 to the exterior wall 133. In some embodiments, ultrasonic and/or laser welding may be used to cause the material of the exterior wall 133 to flow into the pores 138 of the portion of the anti-run-dry membrane 136 that is adjacent to the exterior wall 133. This may be facilitated through the application of pressure that presses the anti-run-dry membrane 136 against the exterior wall 133 prior to and/or during the welding process to encourage flow of melted material of the exterior wall 133 into the pores 138.

Although in FIG. 1, the anti-run-dry membrane 136 is positioned within the drip unit 104, those of skill in the art will recognize that, in alternative embodiments, an anti-run-dry membrane may be positioned elsewhere within an intravenous delivery system. For example, an anti-run-dry membrane may be positioned within the tubing 106 and/or within the intravenous access unit 112. The systems and methods of the present invention may be used to attach such anti-run-dry membranes, as well as those that are positioned within drip units.

Figure 2:
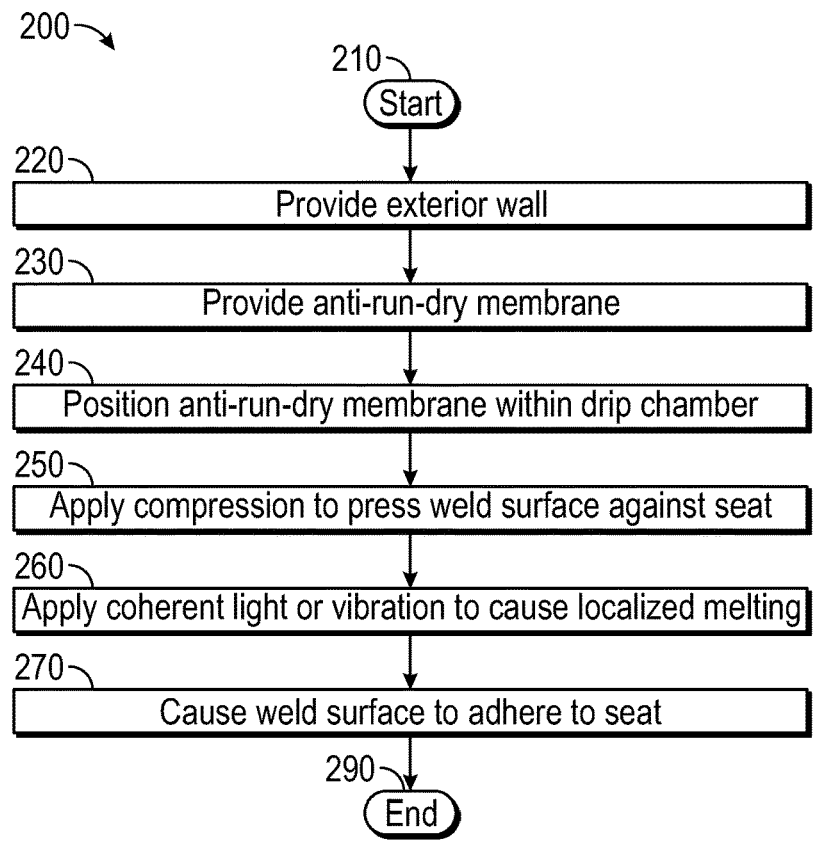
FIG. 2 is a flowchart diagram illustrating a method of manufacturing a drip chamber for an intravenous delivery system, according to one embodiment.

A method 200, in generalized form, of attaching the anti-run-dry membrane 136 to the exterior wall 133 will be provided in connection with FIG. 2. More specific examples will be presented in connection with FIGS. 3-11.

Referring to FIG. 2, a flowchart diagram illustrates a method 200 of manufacturing a drip chamber for an intravenous delivery system, according to one embodiment. The method 200 will be described with reference to the intravenous delivery system 100 of FIG. 1. However, those of skill in the art will recognize that the method 200 may be carried out with different intravenous delivery systems. Similarly, the intravenous delivery system 100 may be manufactured through the use of methods other than that of FIG. 2.

The method 200 may start 210 with a step 220 in which the exterior wall 133 of the drip unit 104 is provided. The exterior wall 133 may be made of a polymer such as PVC, SBC, and TPO, and may be manufactured through the use of various processes, including but not limited to injection molding, blow molding, casting, and/or the like.

In a step 230, the anti-run-dry membrane 136 may be provided. The anti-run-dry membrane 136 may be made of a polymer such as Polyethersulfone (PES), and may be manufactured through the use of the processes listed above, by way of example. The processes used to form the anti-run-dry membrane 136 may be tuned to provide the pores 138 of the anti-run-dry membrane 136 with the desired size, which may be optimized to permit passage of the liquid 122 through the anti-run-dry membrane 136, while limiting passage of air through the anti-run-dry membrane 136.

The step 230 may optionally include any of the methods described above for reducing the melting point of the anti-run-dry membrane 136 to a level close to the melting point of the exterior wall 133. In the alternative, no such methods may be used; rather, subsequent welding processes may be carried out in a manner that facilitates adherence of the anti-run-dry membrane 136 to the exterior wall 133 with a significant disparity in melting points between the exterior wall 133 and the anti-run-dry membrane 136.

In a step 240, the anti-run-dry membrane 136 may be positioned within the drip chamber 134 that is at least partially defined by the exterior wall 133. Other components such as the drip feature 132 may cooperate with the exterior wall 133 to fully define the drip chamber 134. The anti-run-dry membrane 136 may be positioned such that a weld surface of the anti-run-dry membrane 136 is adjacent to and/or in contact with a seat of the exterior wall 133.

In a step 250, compression may be applied to press the weld surface of the anti-run-dry membrane 136 against the seat of the exterior wall 133. In the event that the melting point of the anti-run-dry membrane 136 is significantly different from that of the exterior wall 133, this compression may help the material of the seat flow into the pores 138 of the anti-run-dry membrane 136 that are adjacent to the seat during the welding process. Hence, this compression may continue to be applied during the welding process.

In a step 260, welding may be carried out by applying coherent light and/or vibration to cause localized melting of the seat and/or the weld surface. As will be shown and described subsequently, the coherent light may be emitted by a laser and directed at the juncture between the seat of the exterior wall 133 and the weld surface of the anti-run-dry membrane 136. As will also be shown and described subsequently, the vibration may be applied by an ultrasonic welding horn.

In a step 270, in response to application of the coherent light and/or the vibration, the weld surface may adhere to the seat. As mentioned previously, this may be due to in-flow of material of the seat of the exterior wall 133 into the pores 138 of the anti-run-dry membrane 136 that are adjacent to the seat. The method 200 may then end 290.

The adherence of the anti-run-dry membrane 136 to the exterior wall 133 may occur in a closed pathway that defines a substantially fluid-tight seal between the weld surface and the seat. The seal may cause any liquid or gas moving between an upper portion and a lower portion of the drip chamber to pass through the anti-run-dry membrane 136.

Various systems, procedures, and/or configurations for carrying out the method 200 will be shown and described in detail in FIGS. 3 through 11. More specifically, exemplary laser welding techniques will be shown and described with reference to FIGS. 3 through 6. Exemplary ultrasonic welding techniques will be shown and described with reference to FIGS. 7 through 11.

Figure 3:
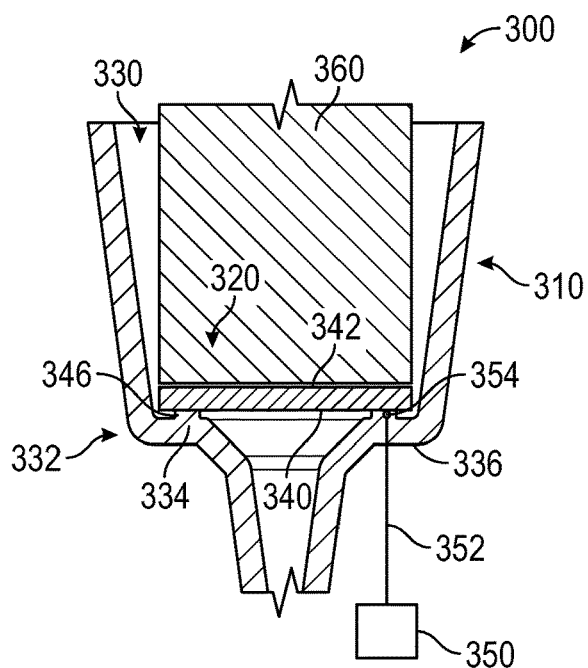
FIG. 3 is a front elevation, section view of a portion of a drip unit according to one embodiment, illustrating the use of a laser to laser weld the anti-run-dry membrane to the exterior wall of the drip unit.

Referring to FIG. 3, a front elevation, section view illustrates a portion of a drip unit 300 according to one embodiment. The drip unit 300 may have an exterior wall 310 and an anti-run-dry membrane 320. The exterior wall 310 may have a cylindrical, frustoconical, and/or other shape that defines a drip chamber 330 that receives the liquid 122. The exterior wall 310 may have a shelf 332 on which a seat 334 is formed, facing toward the anti-run-dry membrane 320. The shelf 332 may also have an opposing surface 336 aligned with the seat 334 and facing outward. The seat 334 need not have any particular geometry, but may instead simply be a flat, annular surface.

The anti-run-dry membrane 320 may have a proximal surface 340 that faces toward the seat 334, and a distal surface 342 that faces away from the seat 334. A subset of the proximal surface 340, such as a peripheral ring, may act as a weld surface 346 that rests against the seat 334 and is to be laser welded to the seat 334.

Welding may be carried out through the use of a laser 350 that projects coherent light 352 at the juncture between the seat 334 and the weld surface 346. The coherent light 352 may be projected at a laser impingement area 354. The coherent light 352 may be projected at the location illustrated in FIG. 3 for sufficient time to cause some of the material of the seat 334 to become flowable. The flowable material of the seat 334 may then flow into the pores 138 of the weld surface 346 to effect adherence of the seat 334 to the weld surface 346 at that location. Once this has been accomplished, the laser impingement area 354 may be moved to a different portion of the juncture between the seat 334 and the weld surface 346 that has not yet been welded. This may be done, for example, by moving the laser impingement area 354 in any of a variety of closed shapes, as will be discussed subsequently.

As mentioned in the description of FIG. 2, compression may be applied to press the weld surface 346 against the seat 334. This may be done, for example, with a fixture 360. The fixture may simply be a cylindrical metal piece. Another fixture (not shown) may be placed on the opposite side of the drip unit 300 to keep the exterior wall 310 in place during the compression and/or welding processes. Such an additional fixture may advantageously avoid occluding any of the pathways taken by the coherent light 352 during the welding process.

The exterior wall 310 may be formed of a generally translucent material. Thus, the coherent light 352 may pass through the opposing surface 336 and through the interior of the shelf 332 to reach the juncture between the seat 334 and the weld surface 346. As shown, the opposing surface 336 may be oriented in a direction substantially perpendicular to the direction along which the coherent light 352 is directed.

This may help to minimize undesired displacement of the laser impingement area 354 due to refraction.

The laser 350 may be designed to produce the coherent light 352 with a wavelength appropriate for causing this localized melting to occur. In some examples, the coherent light 352 may have a relatively large wavelength, i.e., a wavelength that exceeds 2,000 nanometers. Such wavelengths may facilitate laser welding of clear plastics, such as the materials used in the construction of the exterior wall 310 and/or the anti-run-dry membrane 320, without requiring the use of an additive such as an absorber that absorbs the coherent light 352. In alternative embodiments (not shown), a lower wavelength of coherent light may be used in conjunction with such an absorber.

The opposing surface 336 may have a surface roughness that is specifically selected to cause the laser impingement area 354 to have the desired size. If the opposing surface 336 has a smooth finish, it may cause little scattering of the coherent light 352, thereby causing the laser impingement area 354 to be relatively small. Conversely, if the opposing surface 336 has a roughened finish, considerable scattering of the coherent light 352 may occur, causing the laser impingement area 354 to be larger. Having the laser impingement area 354 at the appropriate size is beneficial. Specifically, if the laser impingement area 354 is too small, the material around the laser impingement area 354 may overheat, causing excessive melt flow. Conversely, if the laser impingement area 354 is too large, the material around the laser impingement area 354 may become insufficiently flowable, or material that is not intended to be welded may become flowable, resulting in damage to the exterior wall 310.

In some embodiments, it may be desirable to use a two-piece anti-run-dry membrane to facilitate laser welding and/or ultrasonic welding. One such example will be shown and described in connection with FIG. 4.

Figure 4:
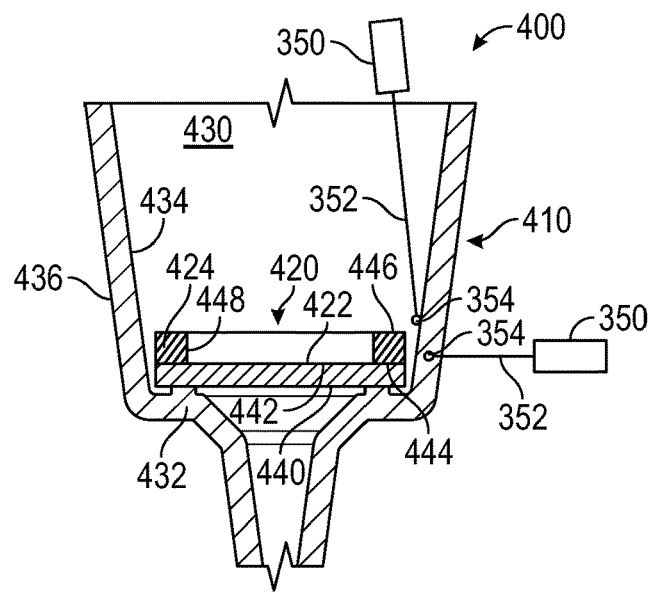
FIG. 4 is a front elevation, section view of a portion of a drip unit according to one alternative embodiment, illustrating the use of one or more lasers to laser weld a two-piece anti-run-dry membrane to the exterior wall of the drip unit.

Referring to FIG. 4, a front elevation, section view illustrates a portion of a drip unit 400 according to one alternative embodiment. The drip unit 400 may have an exterior wall 410 similar to that of the drip unit 300 of FIG. 3, and an anti-run-dry membrane 420 with two-piece construction. The exterior wall 410 may have a cylindrical, frustoconical, and/or other shape that defines a drip chamber 430 that receives the liquid 122. The exterior wall 410 may have a shelf 432, and a seat 434 positioned above the shelf, facing inward toward the anti-run-dry membrane 420. The exterior wall 410 may have an opposing surface 436 aligned with the seat 434 and facing outward.

The anti-run-dry membrane 420 may have a two-piece design. Specifically, the anti-run-dry membrane 420 may have a membrane component 422 that provides the desired liquid permeability and air impermeability, and a welding component 424 that facilitates welding of the anti-run-dry membrane 420 to the exterior wall 410. The membrane component 422 may have a proximal surface 440 that faces toward the shelf 432, and a distal surface 342 that faces away from the shelf 432. The welding component 424 may have a membrane attachment surface 444 and a weld surface 446. The membrane attachment surface 444 may be secured to the distal surface 442 of the membrane component 422, and the weld surface 446 may be secured to the seat 434 via laser welding. The welding component 424 may have an annular shape with a bore 448 passing through its interior.

The membrane attachment surface 444 may be secured to the membrane component 422 in any of a variety of ways. In some embodiments, the membrane attachment surface 444 may be welded to the membrane component 422 through the use of a process such as thermal welding, ultrasonic welding, laser welding, friction welding, and/or the like. Additionally or alternatively, the membrane attachment surface 444 may be secured to the membrane component 422 through the use of other attachment methods such as mechanical fastening, chemical bonding, adhesive bonding, and/or the like. The welding component 424 may be formed of a material that is readily attachable to the membrane component 422 (through the use of one of the attachment methods referenced above) and to the exterior wall 410. In some embodiments, the welding component 424 may be formed of a material with a melting point between those of the membrane component 422 and the exterior wall 410. Thus, the welding component 424 may be readily weldable to both the membrane component 422 and the exterior wall 410.

The weld surface 446 of the welding component 424 may be welded to the seat 434 via laser welding through the use of one or more lasers 350, each of which projects coherent light 352 at a laser impingement area 354. As shown, this may be done by projecting the coherent light 352 along a variety of directions. In some embodiments, the laser 350 may be positioned in-plane with the welding component 424, and the coherent light 352 may be projected along a direction substantially perpendicular to the weld surface 446, through the opposing surface 436, as shown. If desired, the coherent light 352 may be projected along a direction that is not perpendicular to the opposing surface 436. Diffraction of the coherent light 352 may be taken into account in order to determine where the coherent light 352 should be projected in order to cause the laser impingement area 354 to be at the desired location.

In other embodiments, the laser 350 may be positioned to project the coherent light 352 directly at the juncture between the seat 434 and the weld surface 446. This may be done, for example, by positioning the laser 350 above the welding component 424, as also shown. In such an embodiment, the size of the laser impingement area 354 may not be determined by the surface roughness of the exterior wall 410. If desired, various optical components, such as lenses, diffusers, and/or the like, may be used to cause the laser impingement area 354 to have the desired size.

The attachment of the welding component 424 to the membrane component 422 may define a seal with the membrane component 422, about the entire circumference of the membrane attachment surface 444. Further, the laser welding of the seat 434 to the weld surface 446 may define a seal between the welding component 424 and the seat 434, about the entire circumference. Thus, in order to pass from the upper portion of the drip chamber 430 to the lower portion of the drip chamber 430, fluids may have to pass through the bore 448 and through the membrane component 422, which may serve as a barrier to air passage as described above.

As mentioned previously, a laser impingement area may be moved along any of a variety of closed paths in order to form the seal between an anti-run-dry membrane (whether a one-piece anti-run-dry membrane or a differently configured anti-run-dry membrane such as a two-piece anti-run-dry membrane) and an exterior wall. Exemplary paths will be shown and described in connection with FIGS. 5 through 6D.

Figure 5:
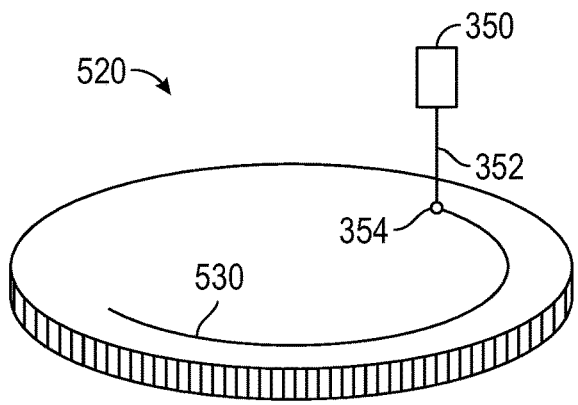
FIG. 5 is a perspective view of an anti-run-dry membrane, illustrating the use of a laser to laser weld the anti-run-dry membrane in place by moving the laser impingement area along a circular path.

Referring to FIG. 5, a perspective view illustrates an anti-run-dry membrane 520. FIG. 5 illustrates the use of a laser 350 to laser weld the anti-run-dry membrane 520 in place by projecting coherent light 352 at a laser impingement area 354 on the surface of the anti-run-dry membrane

520. The laser impingement area 354 may be moved along a circular path 530. The circular path 530 may extend full-circle so that the entire circumference of the anti-run-dry membrane 520 is welded in place, thereby defining a seal with the associated exterior wall (not shown).

Notably, the laser impingement area 354 may be moved in a variety of ways. If desired, the laser 350 may be moved in a circular pattern relative to the anti-run-dry membrane 520, without significantly changing the angle at which the coherent light 352 impinges on the anti-run-dry membrane 520. Alternatively, the laser 350 may remain stationary relative to the anti-run-dry membrane 520, and may change orientations to project the coherent light 352 along the direction needed to position the laser impingement area 354 at the desired location on the circular path 530. In such examples, the coherent light 352 may not be directed perpendicular to the surface of the anti-run-dry membrane 520, but may instead impinge on the surface of the anti-run-dry membrane 520 from along various other angles. The relative motion mentioned above may be provided by moving either of the laser 350 and the anti-run-dry membrane 520, while keeping the other stationary.

Various other paths may be used to provide a seal. Examples of such paths will be shown and described in connection with FIGS. 6A through 6D, as follows.

Referring to FIGS. 6A through 6D, plan views illustrate various paths that may be followed by a laser impingement area in order to secure an anti-run-dry membrane in place. Each of these Figures illustrates a closed pathway by which laser welding may be used to form a seal.

Figure 6A:
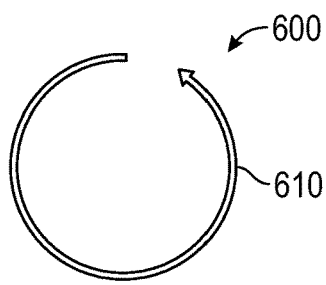
FIGS. 6A-6D are plan views of various paths that may be followed by a laser impingement area in order to secure an anti-run-dry membrane in place.

FIG. 6A illustrates a welding pattern 600 that includes a circular path 610, like the circular path 530 of FIG. 5. As in FIG. 5, the circular path 610 may be a closed pathway, with an endpoint that is substantially the same as the starting point.

Figure 6B:
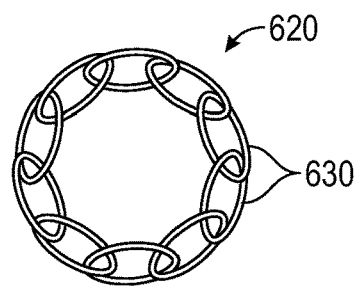

FIG. 6B illustrates a welding pattern 620 that includes a plurality of paths 630, which may be placed adjacent to each other to define a circular pattern. Each of the paths 630 may have a circular, elliptical, or other closed shape. The paths 630 may all be followed by a single laser, or alternatively, each path 630 may be followed by one laser to expedite the time needed to carry out welding. As shown, the paths 630 may overlap slightly to ensure that there are no gaps between them that could otherwise cause an incomplete seal to form.

In addition to expediting manufacturing, the paths 630 may provide an effectively wider weld area, with redundant sealing. Thus, if for some reason, a portion of one of the paths 630 does not form a proper sealed weld (i.e., a weld that does not extend in a fully-closed shape), fluid may still be unable to flow through the remainder of the path 630, as long as there are no other breaks in the path 630. Thus, the welding pattern 620 of FIG. 6B may be relatively forgiving of defects in the welding process. The sizes and shapes of the paths are merely exemplary and may be exaggerated in FIG. 6B for clarity; the paths 630 may be made narrow enough that they are accommodated by the geometry of the weld surface and seat to be welded together.

Figure 6C:
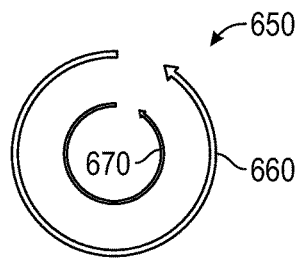

FIG. 6C illustrates a welding pattern 650 that includes a first circular path 660 and a second circular path 670 parallel to the first circular path 660. The second circular path 670 may be nested within the interior of the first circular path 660. Thus, the first circular path 660 and the second circular path 670 may cooperate to define two concentric circles.

Like the welding pattern 620 of FIG. 6B, the welding pattern of FIG. 6C may be relatively forgiving of breaks in the weld. For example, if either of the first circular path 660 or the second circular path 670 has a break, the welding pattern 650 may still maintain a seal as long as the other of the first circular path 660 and the second circular path 670 is unbroken. Further, the welding pattern 650 may provide welding along a relatively wide area. The relative sizes of the first circular path 660 and the second circular path 670 are exaggerated for clarity; the first circular path 660 and the second circular path 670 may be close enough together that they are both accommodated by the geometry of the weld surface and seat to be welded together.

Figure 6D:
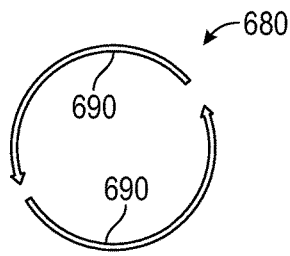

FIG. 6D illustrates a welding pattern 680 that includes two semicircular paths 690. The semicircular path 690 may be arranged head-to-tail such that they cooperate to define a circle. The resulting weld may be similar to that provided by the welding pattern 600 of FIG. 6A. However, the welding pattern 680 may be easily carried out with two lasers, positioned diametrically opposite to each other across the center of the welding pattern 680. Thus, the time required to complete the weld may be reduced to approximately half that of the welding pattern 600 of FIG. 6A.

The welding pattern 600, the welding pattern 620, the welding pattern 650, and the welding pattern 680 are provided merely by way of example. Those of skill in the art, with the aid of the present disclosure, will recognize that a variety of other welding patterns may be used to provide the desired balance between seal integrity and welding speed. Further, these welding patterns relate to an embodiment in which the weld is to be performed on a planar welding juncture, as in the embodiment of FIG. 3. Those of skill in the art, with the aid of the present disclosure, will recognize that the welding pattern 600, the welding pattern 620, the welding pattern 650, and/or the welding pattern 680 may be modified in various ways to form a weld at a non-planar juncture like that of FIG. 4.

Many other configurations and methods may be used to laser weld an anti-run-dry membrane to a chamber wall of a drip unit. Further, other welding methods may be applied in addition to or in the alternative to laser welding. One such method is ultrasonic welding. Various configurations and methods of ultrasonically welding an anti-run-dry membrane to a chamber wall of a drip unit will be shown and described in connection with FIGS. 7 through 11.

Figure 7:
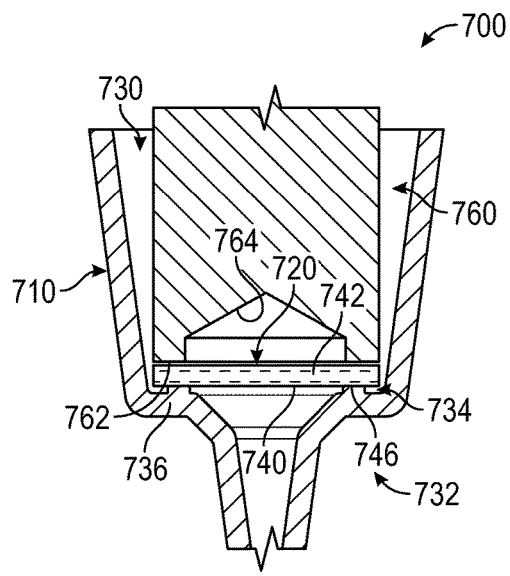
FIG. 7 is a front elevation, section view of a drip unit according to one alternative embodiment, illustrating the use of an ultrasonic welding horn to ultrasonically weld an anti-run-dry membrane to the exterior wall of a drip unit.

Referring to FIG. 7, a front elevation, section view illustrates a drip unit 700 according to one alternative embodiment. The drip unit 700 may have an exterior wall 710 and an anti-run-dry membrane 720. The exterior wall 710 may have a cylindrical, frustoconical, and/or other shape that defines a drip chamber 730 that receives the liquid 122. The exterior wall 710 may have a shelf 732 on which a seat 734 is formed, facing toward the anti-run-dry membrane 720. The seat 734 may have an energy director 736 formed thereon. The energy director 736 may protrude from the shelf 732 toward the anti-run-dry membrane 720.

The anti-run-dry membrane 720 may have a proximal surface 740 that faces toward the seat 734, and a distal surface 742 that faces away from the seat 734. A subset of the proximal surface 740, such as a peripheral ring, may act as a weld surface 746 that rests against the seat 734 and is to be ultrasonically welded to the seat 734.

The weld surface 746 may be ultrasonically welded to the seat 734 through the use of an ultrasonic welding horn 760. The ultrasonic welding horn 760 may have a generally cylindrical shape sized to fit into the interior of the exterior wall 710. The ultrasonic welding horn 760 may have a welding rim 762 with an annular shape, and a relief 764 interior to the welding rim 762.

The compression referenced in the step 250 of the method 200 of FIG. 2 may be provided by the ultrasonic welding horn 760. Specifically, the ultrasonic welding horn 760 may be pressed against the distal surface 742 of the anti-run-dry membrane 720 with a predetermined force, thereby compressing the weld surface 746 against the energy director 736 of the seat 734. The ultrasonic welding horn 760 may be coupled to a vibration source, such as an eccentric motor, electromagnet, or the like. As the welding rim 762 compresses the weld surface 746 against the seat 734, the vibration source may cause the ultrasonic welding horn 760 to vibrate at a frequency appropriate for causing localized melting of the material of the weld surface 746 and/or the material of the shelf 732. Such a frequency may be, for example, 15 kHz, 20 kHz, 30 kHz, 35 kHz, 40 kHz, or 70 kHz. The welding that occurs as a result will be shown and described in connection with FIGS. 8A through 8C.

Figure 8A:
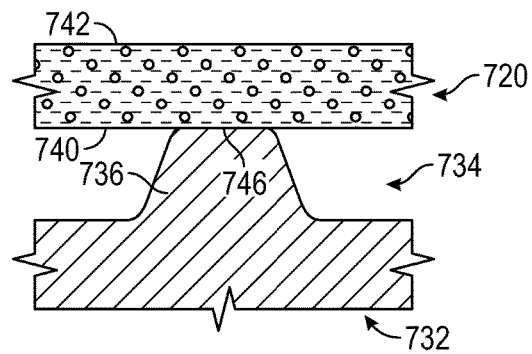
FIGS. 8A-8C are front elevation, section views of the seat of the exterior wall and the weld surface of the anti-run-dry membrane of FIG. 7, in an uncompressed state, a compressed state, and a welded state, respectively.
Figure 8B:
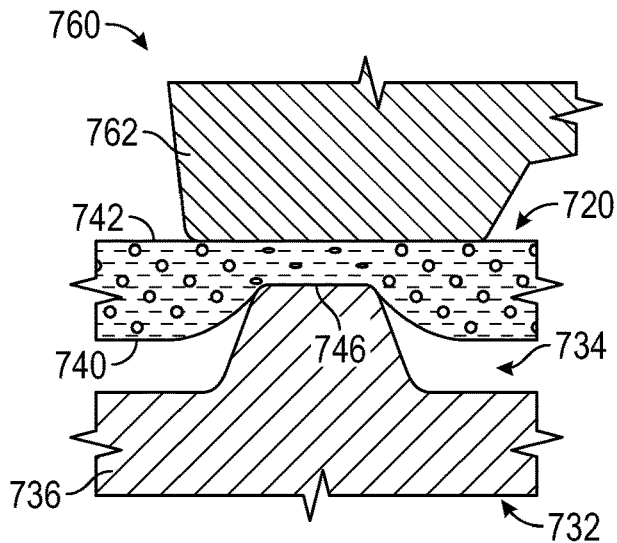
Figure 8C:
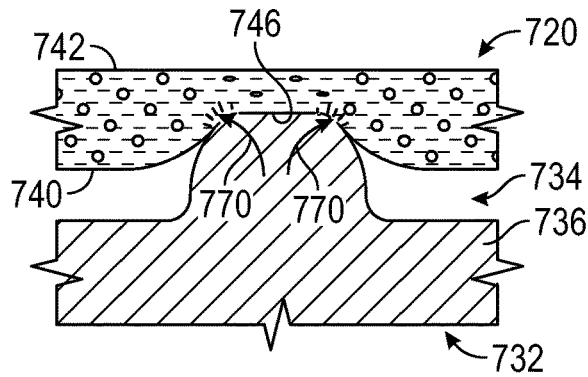

Referring to FIGS. 8A through 8C, front elevation, section views illustrate the seat 734 of the exterior wall 710 and the weld surface 746 of the anti-run-dry membrane 720 of FIG. 7, in an uncompressed state, a compressed state, and a welded state, respectively. These Figures illustrate the manner in which welding occurs in response to the compression and/or vibration provided by the ultrasonic welding horn 760.

FIG. 8A illustrates the juncture between the seat 734 and the weld surface 746 prior to application of compression from the ultrasonic welding horn 760. As shown, the weld surface 746 of the anti-run-dry membrane 720 may rest on the energy director 736 of the seat 734, in a generally uncompressed state.

FIG. 8B illustrates the juncture between the seat 734 and the weld surface 746 after application of compression from the ultrasonic welding horn 760. The portion of the anti-run-dry membrane 720 adjacent to the energy director 736 may be compressed between the energy director 736 and the welding rim 762 of the ultrasonic welding horn 760. In this state, vibration may be conveyed to the weld surface 746 and the energy director 736 via the welding rim 762. The geometry of the seat 734 may cause the vibration to be relatively intense in the energy director 736, causing melting of the energy director 736 to preferentially occur.

FIG. 8C illustrates the juncture between the seat 734 and the weld surface 746 after completion of the welding process and removal of the ultrasonic welding horn 760. During welding, melted, flowable portions of the energy director 736 may flow into the pore 138 of the anti-run-dry membrane 720 that are adjacent to the weld surface 746. This flow of material may occur along the directions indicated by the arrows 770. After cessation of vibration, the material of the energy director 736 within the pores 138 may solidify, causing the weld surface 746 to adhere to the seat 734, as shown.

The geometry of the seat 734 and the weld surface 746 of FIGS. 7 through 8D is merely exemplary. Alternative geometries may be employed to alter the way in which welding occurs to provide a desired balance between weld strength, weld consistency, and welding time. Other exemplary geometries will be shown and described in connection with FIGS. 9-11.

Figure 9:
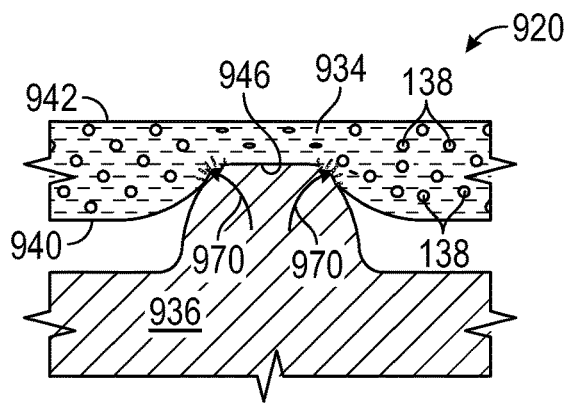
FIG. 9 is a front elevation, section view of a seat of an exterior wall and a weld surface of an anti-run-dry membrane according to one alternative embodiment.

Referring to FIG. 9, a front elevation, section view illustrates a seat 934 of an exterior wall and a weld surface 946 of an anti-run-dry membrane 920 according to one alternative embodiment. The seat 934 may be positioned on a shelf or other feature (not shown) of the exterior wall. The seat 934 may have a configuration similar to that of the seat 734 of FIG. 7, and may thus have an energy director 936 that may serve as a focal point for ultrasonic vibration, and hence, a preferential melting location.

The anti-run-dry membrane 920 may have a configuration different from that of the anti-run-dry membrane 720 of FIGS. 7 through 8C. More precisely, the anti-run-dry membrane 920 may have a proximal surface 940 and a distal surface 942 that have different properties. The proximal surface 940 may have a configuration similar to that of the proximal surface 740 of the previous embodiment. Proximate the proximal surface 940, the anti-run-dry membrane 920 may have pores 138 that are relatively small. However, the distal surface 942 may, if desired, have a roughened surface by comparison with the proximal surface 940. Additionally or alternatively, proximate the distal surface 942, the pores 138 may be relatively large.

This configuration of the anti-run-dry membrane 920 may facilitate secure welding of the weld surface 946 to the seat 934. If the distal surface 942 is roughened, the additional surface features may provide additional surface area for infiltration and/or adherence of the flowable material of the energy director 936 during the welding process. Similarly, if the pores 138 proximate the distal surface 942 are relatively more coarse (i.e., larger), they may receive the flowable material of the energy director 936 in greater quantities during welding, as shown by the arrows 970, resulting in more secure adherence. Hence, the asymmetrical nature of the anti-run-dry membrane 920 may facilitate welding to the seat 934, while enabling the anti-run-dry membrane 920 to serve as a barrier to airflow, as desired. The anti-run-dry membrane 920 may thus facilitate ultrasonic welding through methods such as that discussed in conjunction with FIG. 7, or may also facilitate different modes of attaching the anti-run-dry membrane 920 to an exterior wall.

The anti-run-dry membrane 920 represents only one of many possible embodiments in which the properties of an anti-run-dry membrane are spatially varied to facilitate attachment of the anti-run-dry membrane to an exterior wall. In some exemplary embodiments (not shown), an anti-run-dry membrane may have proximal and distal surfaces that have substantially the same (coarse) pore size, with smaller pores toward the center of the anti-run-dry membrane.

In other alternative embodiments, the geometry of the seat of the exterior wall may be altered to facilitate secure welding. One such embodiment will be shown and described in connection with FIGS. 10A and 10B, as follows.

Figure 10A:
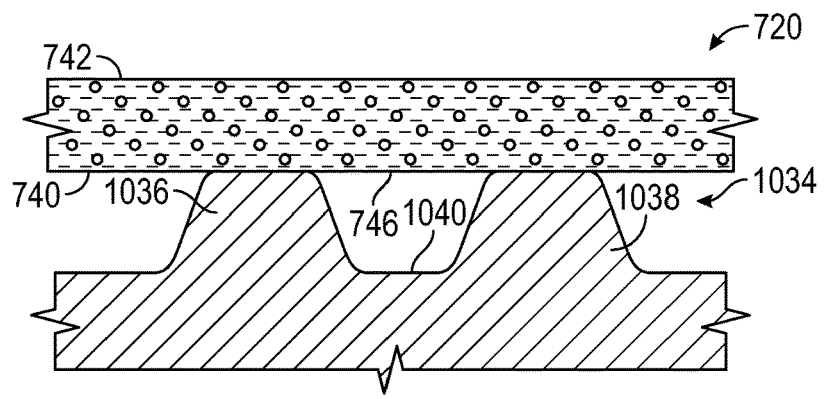
FIGS. 10A and 10B are front elevation, section views of a seat of an exterior wall and a weld surface of an anti-run-dry membrane according to another alternative embodiment, prior to and during welding, respectively.
Figure 10B:
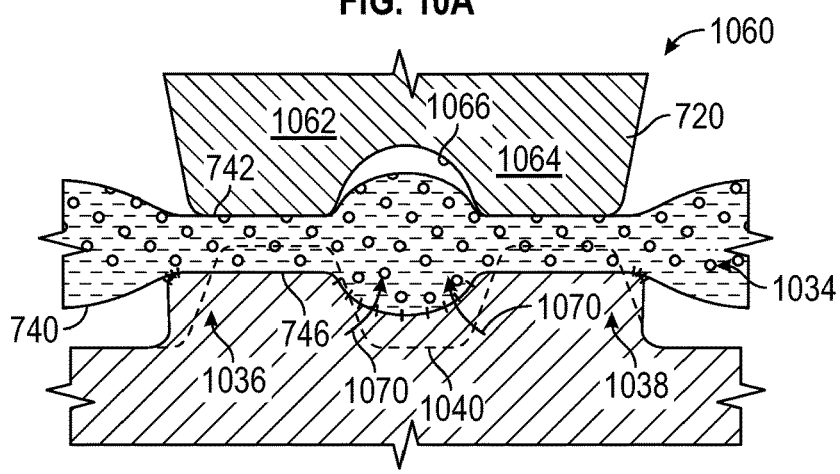

Referring to FIGS. 10A and 10B, front elevation, section views illustrate a seat 1034 of an exterior wall and a weld surface 746 of an anti-run-dry membrane 720 according to another alternative embodiment, prior to and during welding, respectively. The anti-run-dry membrane 720 may be similar to that of FIG. 7, and may thus have a proximal surface 740 and a distal surface 742, with a portion of the proximal surface 740 acting as a weld surface 746. The seat 1034 may be positioned on a shelf or other feature of an exterior wall (not shown).

As illustrated in FIG. 10A, the seat 1034 may have a first energy director 1036 and a second energy director 1038. Like the first energy director 1036, the second energy director 1038 may protrude toward the proximal surface 740 of the anti-run-dry membrane 720. The first energy director 1036 and the second energy director 1038 may be separated by a central relief 1040. As the anti-run-dry membrane 720 is put into place, it may be placed on the distal surfaces of the first energy director 1036 and the second energy director 1038.

As illustrated in FIG. 10B, an ultrasonic welding horn 1060 may be used to provide compression and vibration to ultrasonically weld the anti-run-dry membrane 720 to the seat 1034. The ultrasonic welding horn 1060 may have a first welding rim 1062 and a second welding rim 1064 displaced from the first welding rim 1062, and separated from the first welding rim 1062 by a central relief 1066. The ultrasonic welding horn 1060 may be moved into engagement with the distal surface 742 of the anti-run-dry membrane 720 such that the first welding rim 1062 is aligned with the first energy director 1036, and the second welding rim 1064 is aligned with the second energy director 1038, as shown. Similarly, the central relief 1066 of the ultrasonic welding horn 1060 may be aligned with the central relief 1040 of the seat 1034.

In response to application of the vibration, the material at the edges of the first energy director 1036 and the second energy director 1038 may become flowable and enter the pores 138 of the anti-run-dry membrane 720, as in previous embodiments. Further, the presence of the central relief 1066 in the ultrasonic welding horn 1060 may cause the material of the anti-run-dry membrane 720 between the central relief 1066 and the central relief 1040 to be under less compression than the surrounding material. As a result, material of the seat 1034 may flow into the central relief 1040 and engage the adjoining portion of the weld surface 746 of the anti-run-dry membrane 720, as shown by the arrows 1070. This may provide additional mechanical overlap between the anti-run-dry membrane 720 and the seat 1034, thereby enhancing the strength of adherence between the anti-run-dry membrane 720 and the seat 1034.

As indicated previously, the exterior wall of a drip unit, such as the exterior wall 710 of FIG. 7, may be formed through the use of injection molding or the like. Forming protrusions such as the energy director 736 of FIGS. 7 and 8, the energy director 936 of FIG. 9, and the first energy director 1036 and the second energy director 1038 of FIG. 10 may be pose unique challenges for injection molding, particularly if they are displaced significantly from the gate at which the molten plastic enters the mold. Accordingly, it may be advantageous to use an energy director with an alternative configuration. One such alternative configuration will be shown and described in connection with FIG. 11.

Figure 11:
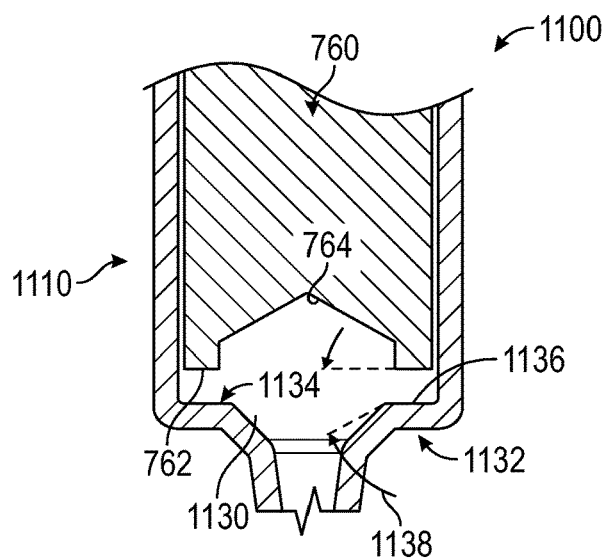
FIG. 11 is a front elevation, section view of a drip unit according to one alternative embodiment, illustrating the use of an ultrasonic welding horn to ultrasonically weld an anti-run-dry membrane to the exterior wall of the drip unit.

Referring to FIG. 11, a front elevation, section view illustrates a drip unit 1100 according to one alternative embodiment. The drip unit 1100 may have an exterior wall 1110 and an anti-run-dry membrane 720, which may be similar to that of FIG. 7, and has been omitted from FIG. 11 for clarity. The exterior wall 1110 may have a cylindrical, frustoconical, and/or other shape that defines a drip chamber 1130 that receives the liquid 122. The exterior wall 1110 may have a shelf 1132 on which a seat 1134 is formed, facing toward the anti-run-dry membrane 720. The seat 1134 may take the form of a tapered surface.

More specifically, the seat 1134 may have a generally frustoconical shape angled at an angle 1138 relative to the welding rim 762 of the ultrasonic welding horn 760. The seat 1134 may have a leading edge 1136 positioned toward the ultrasonic welding horn 760. The ultrasonic welding horn 760 may be configured like that of FIG. 7, and may be used to apply compression to and ultrasonically weld the anti-run-dry membrane 720 to the seat 1134. The ultrasonic welding horn 760 may contact the edge 1136 and transmit compression and vibration directly to the leading edge 1136. The compression and vibration may be concentrated in the leading edge 1136, which may act as an energy director. Hence, the leading edge 1136 may undergo preferential melting, and flow into the pores 138 of the weld surface 746 of the anti-run-dry membrane 720.

Advantageously, the seat 1134 has no protruding parts. Thus, the exterior wall 1110 may have a shape that is readily formed via injection molding, even if the seat 1134 is displaced significantly from the gate of the mold. The absence of blind pockets may help avoid the occurrence of gas traps and unpacked parts in the injection molding process. Those of skill in the art will recognize, with the aid of the present disclosure, that a wide variety of other seat geometries may be used to facilitate welding of anti-run-dry membranes without encumbering the injection molding process used to form the exterior wall.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A method for manufacturing a drip unit for an intravenous delivery system, the method comprising:
   providing an exterior wall shaped to at least partially define a drip chamber capable of receiving a liquid from a liquid source, the exterior wall comprising a seat;
   providing an anti-run-dry membrane comprising a plurality of pores that are permeable to the liquid, wherein the anti-run-dry membrane is formed of a hydrophilic material configured to resist passage of air through the pores, the anti-run-dry membrane comprising a weld surface;
   positioning the anti-run-dry membrane within the drip chamber such that the weld surface is in contact with the seat;
   applying compression to press the weld surface against the seat;
   applying at least one selection from the group consisting of coherent light and vibration to at least one of the anti-run-dry membrane and the exterior wall to cause localized melting of at least one of the seat and the weld surface; and
   in response to the localized melting, causing the weld surface to adhere to the seat.

2. The method of claim 1, wherein providing the anti-run-dry membrane comprises:
   providing a hydrophilic material comprising a base material melting point;
   performing a melting point reduction procedure on the hydrophilic material; and
   forming the anti-run-dry membrane such that, due to performance of the melting point reduction procedure, the anti-run-dry membrane has a membrane melting point significantly lower than the base material melting point;
   wherein the membrane melting point is within 20° C. of a wall melting point of the exterior wall.

3. The method of claim 2, wherein performing the melting point reduction procedure comprises changing a chemical composition of a pre-polymer used to form the hydrophilic material to increase flexibility of a chemical structure of the pre-polymer.

4. The method of claim 2, wherein performing the melting point reduction procedure comprises copolymerizing the hydrophilic material with an additive such that, in combination, the hydrophilic material and the additive have a combined chemical structure more flexible than a base chemical structure of the hydrophilic material.

5. The method of claim 2, wherein performing the melting point reduction procedure comprises adding side branching to an aromatic ring structure of the hydrophilic material, thereby increasing flexibility of the aromatic ring structure.

6. The method of claim 1, wherein the anti-run-dry membrane comprises a membrane melting point at least 20° C. higher than a wall melting point of the exterior wall, wherein causing the weld surface to adhere to the seat comprises:
 causing flowable portions of the seat to enter the pores of the weld surface; and
 permitting the flowable portions to solidify within the pores.

7. The method of claim 1, wherein applying the compression comprises using a fixture to apply the compression, wherein applying the selection comprises, during application of the compression, applying the coherent light via a laser.

8. The method of claim 7, wherein the coherent light comprises a wavelength greater than 2,000 nanometers.

9. The method of claim 7, wherein applying the coherent light comprises:
 directing the coherent light to a laser impingement area proximate a juncture between the seat and the weld surface; and
 moving the laser impingement area along the juncture, in a closed pathway;
 wherein causing the weld surface to adhere to the seat comprises causing the weld surface adhere to the seat along the pathway to provide a seal between the seat and the weld surface;
 wherein the seal is positioned to cause fluid flowing from an upper part of the drip chamber to a lower part of the drip chamber to flow through the anti-run-dry membrane.

10. The method of claim 7, wherein the exterior wall further comprises an opposing surface aligned with the seat and facing exterior to the exterior wall, wherein applying the coherent light via the laser comprises directing the coherent light at the seat through the opposing surface, along a direction substantially perpendicular to the opposing surface.

11. The method of claim 10, wherein applying the coherent light comprises:
 determining an optimal size of a laser impingement area proximate a juncture between the seat and the weld surface; and
 determining a surface roughness level of the opposing surface that will cause the laser impingement area to have the optimal size;
 wherein providing the exterior wall comprises forming the opposing surface with the surface roughness level;
 wherein applying the coherent light comprises directing the coherent light to the laser impingement area, the laser impingement area.

12. The method of claim 7, wherein the anti-run-dry membrane comprises a membrane component and a welding component having a substantially rigid construction, wherein the membrane component comprises the pores and the welding component comprises the weld surface.

13. The method of claim 1, wherein applying the compression comprises using an ultrasonic welding horn to apply the compression, wherein applying the selection comprises, during application of the compression, applying the vibration via the ultrasonic welding horn.

14. The method of claim 13, wherein the anti-run-dry membrane comprises a weld surface pore size of the pores proximate the weld surface, and a displaced pore size of the pores displaced from the weld surface, wherein the weld surface pore size is significantly larger than the displaced pore size.

15. The method of claim 13, wherein providing the exterior wall comprises forming a first energy director on the seat, wherein the first energy director is shaped to protrude toward a location at which the anti-run-dry membrane will reside, relative to the exterior wall;
 wherein positioning the anti-run-dry membrane within the drip chamber comprises positioning the weld surface in contact with the first energy director.

16. The method of claim 15, wherein providing the exterior wall further comprises forming a second energy director on the seat, displaced from the first energy director such that the seat comprises a seat channel positioned between the first energy director and the second energy director, wherein the second energy director is shaped to protrude toward the location;
 wherein positioning the anti-run-dry membrane within the drip chamber comprises positioning the weld surface in contact with the second energy director;
 wherein the ultrasonic welding horn comprises a horn channel;
 wherein using the ultrasonic welding horn to apply the compression comprises:
  aligning the horn channel with the seat channel; and
  urging the ultrasonic welding horn against the weld surface and the seat;
 wherein causing the weld surface to adhere to the seat comprises causing a flowable portion of the weld surface to flow into the seat channel.

17. The method of claim 13, wherein providing the exterior wall comprises providing the seat with a tapered shape comprising a leading edge, wherein using the ultrasonic welding horn to apply the compression comprises urging the ultrasonic welding horn against the leading edge;
 wherein, during application of the vibration, the leading edge acts as an energy director by facilitating initiation of melt flow of the seat at the leading edge.

18. A method for manufacturing a drip unit for an intravenous delivery system, the method comprising:
 providing an exterior wall shaped to at least partially define a drip chamber capable of receiving a liquid from a liquid source, the exterior wall comprising a seat;
 providing an anti-run-dry membrane comprising a plurality of pores that are permeable to the liquid, wherein the anti-run-dry membrane is formed of a hydrophilic material configured to resist passage of air through the pores, the anti-run-dry membrane comprising a weld surface;
 positioning the anti-run-dry membrane within the drip chamber such that the weld surface is in contact with the seat;
 with a laser, directing coherent light to a laser impingement area proximate a juncture between the seat and the weld surface;
 moving the laser impingement area along the juncture, in a closed pathway such that the weld surface adheres to the seat along the pathway; and
 in response to motion of the laser impingement area along the juncture, causing the weld surface to adhere to the seat along the pathway to provide a seal between the seat and the weld surface, wherein the seal is positioned to cause fluid flowing from an upper part of the drip chamber to a lower part of the drip chamber to flow through the anti-run-dry membrane.

19. A method for manufacturing a drip unit for an intravenous delivery system, the method comprising:
providing an exterior wall shaped to at least partially define a drip chamber capable of receiving a liquid from a liquid source, the exterior wall comprising a seat;
providing an anti-run-dry membrane comprising a plurality of pores that are permeable to the liquid, wherein the anti-run-dry membrane is formed of a hydrophilic material configured to resist passage of air through the pores, the anti-run-dry membrane comprising a weld surface;
positioning the anti-run-dry membrane within the drip chamber such that the weld surface is in contact with the seat;
moving an ultrasonic welding horn into contact with at least one of the anti-run-dry membrane and the exterior wall; and
with the ultrasonic welding horn, applying vibration to at least one of the seat and the weld surface;
in response to application of the vibration, causing the weld surface to adhere to the seat.

20. The method of claim 19, wherein the anti-run-dry membrane is formed of a hydrophilic material;
wherein the anti-run-dry membrane comprises a membrane melting point that is within 20° C. of a wall melting point of the exterior wall;
wherein providing the exterior wall comprises providing the seat with a tapered shape comprising a leading edge, wherein moving the ultrasonic welding horn into contact with at least one of the anti-run-dry membrane and the exterior wall comprises urging the ultrasonic welding horn against the leading edge;
wherein, during application of the vibration, the leading edge acts as an energy director by facilitating initiation of melt flow of the seat at the leading edge.

* * * * *